United States Patent [19]

Speidel

[11] Patent Number: 4,667,924
[45] Date of Patent: May 26, 1987

[54] AIR RELEASE VALVE FOR SPHYGMOMANOMETERS AND THE LIKE

[76] Inventor: Blasius Speidel, Hochmeisterstrasse 33, 7455 Jungingen, Fed. Rep. of Germany

[21] Appl. No.: 724,554

[22] Filed: Apr. 18, 1985

[30] Foreign Application Priority Data

Apr. 18, 1984 [DE] Fed. Rep. of Germany ....... 3414709

[51] Int. Cl.⁴ ............................................. F16L 55/14
[52] U.S. Cl. ............................................. 251/9; 251/7
[58] Field of Search ............................ 251/4, 5, 7–10; 128/677, 685

[56] References Cited

U.S. PATENT DOCUMENTS

| 3,167,085 | 1/1965 | Redmer | 251/8 |
| 3,221,943 | 12/1965 | Anderson | 251/9 |
| 3,460,526 | 8/1969 | McKirdy et al. | 128/674 |
| 3,544,060 | 12/1970 | Stoltz et al. | 251/9 |
| 3,779,236 | 12/1973 | Stewart | 128/685 |
| 3,840,207 | 10/1974 | Carpenter, Jr. | 251/5 |
| 4,044,989 | 8/1977 | Basel et al. | 251/7 |
| 4,146,018 | 3/1979 | Aldridge et al. | 128/685 |
| 4,354,660 | 10/1982 | Stupar et al. | 251/4 |
| 4,491,156 | 1/1985 | Lee, II | 251/7 |

FOREIGN PATENT DOCUMENTS

| 2759119 | 8/1978 | Fed. Rep. of Germany |  |
| 3241939 | 5/1983 | Fed. Rep. of Germany |  |
| 2076941 | 12/1980 | United Kingdom | 128/685 |

Primary Examiner—Martin P. Schwadron
Assistant Examiner—Sheri M. Novack
Attorney, Agent, or Firm—Joseph A. Geiger

[57] ABSTRACT

An air release valve for sphygmomanometers in the form of a flow metering device in an air outlet duct comprising a length of a flexible tube as part of said duct and a pressure member which is displaceable against the valve tube by means of a pivot lever, so as to collapse one tube wall against the other to close the cavity of the valve tube and to produce an initially very gradual and later progressively greater opening response, when the pressure member is retracted and the valve tube is allowed to return to its open state. The valve tube may be an arcuate tube portion extending freely between two parallel spouts of the air outlet duct, or it may be a straight tube portion confined in a longitudinal groove of the valve housing. A U-shaped leaf spring between the valve housing and the pivot lever provides a valve closing force, finger pressure against the pivot lever produces a controlled valve opening action.

18 Claims, 20 Drawing Figures

AIR RELEASE VALVE FOR SPHYGMOMANOMETERS AND THE LIKE

BACKGROUND OF THE INVENTION

1. Field of the Invention

The present invention relates to blood pressure measuring devices or sphygomanometers and, more particularly, to a valve for the controlled release of the air from the pressurized measuring cuff of a sphygomanometer during the taking of blood pressure measurements.

2. Description of the Prior Art

The taking of blood pressure measurements by the method of Riva-Rocci and Korotkoff involves the use of an inflatable measuring cuff which is wrapped around an extremity of a person and inflated to a pressure level above the anticipated systolic blood pressure reading by means of a source of air pressure. The pressure inside the measuring cuff is then reduced in a delicately adjusted and as even as possible way, so that, when the systolic blood pressure value is approached, the onset of the so-called Korotkoff noises in the blood flow can be detected acoustically and, later, at the diastolic blood pressure value, the disappearance of these blood flow noises is reliably detected. For this purpose, an air release valve is arranged in the connecting hose between the measuring cuff and the pressure source, the air release valve comprising a flow metering device for the pressurized air, as the latter exits to the atmosphere via an outlet duct.

The various known air release valves include simple valves which have a release screw with a conical extremity that serves as a valve body in cooperation with a matchingly tapered valve seat. A disadvantage of this type of air release valve is its ergonomically unfavorable adjustment movement which requires considerable finger dexterity and skill on the part of the operator. Other known air release valves have a valve body with a very slender valve cone which cooperates with a cylindrical or likewise tapered valve seat. The valve cone is moved by means of a finger, using either a sliding lever or a pivoting lever. Both versions have the shortcoming that, in the course of the opening adjustments of the valve cone, which normally involve a linear displacement, the cross-sectional area increases as a square function of the valve displacement. Accordingly, the relatively rapid increase in the cross sectional area results in the setting of air release speeds of different magnitude, caused by uneven adjustment displacements of the valve cone, as may be necessary, for instance, in the course of measuring the interior pressure or under non-uniform initial pressure levels. The sensitivty of these air release valves is therefore not uniform over their entire operational range.

SUMMARY OF THE INVENTION

Underlying the present invention is the objective of conceiving an air release valve which makes possible the metering of the pressure reduction in as even a manner as possible over it entire operating range.

This objective is attained with an air release valve in which a valve tube which extends between two connecting spouts in a free arc, is collapsed within the plane of its arcuate portion by means of a pressure member under the influence of a valve closing force. At the same time, the upper tube wall of the arcuate portion is deformed inwardly in the plane which is perpendicular to the plane of the arcuate portion and pressed against the lower tube wall of the arcuate portion, so as to completely close the cavity of the valve tube at this point. The operation of the valve adjustment lever causes the pressure member to be lifted from the valve tube to a greater or lesser extent, in opposition to the valve closing force, so that, on the one hand, the upper tube wall is lifted from the lower tube wall to a correspondingly greater or lesser extent and, on the other hand, the collapsed arcuate portion is allowed to return in a greater or lesser degree to its original arcuate shape. It follows that the cavity of the valve tube is opened to a correspondingy greater or lesser extent, so that air can escape from the air duct at a corresponding rate. Due to the fact that, under the pressure of the pressure member, the upper tube wall on the arcuate portion of the valve tube is deflected inwardly beyond the flat shape, and both its cross-sectional shape and its arcuate shape assume a negative curvature, the lower tube wall serves as a kind of trough with a spatially curved surface against which the upper tube wall abuts under intimate contact. The results of this considerable elastic deformation of the upper and lower tube walls are, on the one hand, an excellent closing seal inside the valve tube in the closed position of the pressure member and, on the other hand, a comparatively long deformation movement of the collapsed tube walls which is accompanied, particularly at the first stage of the return movement to the normal shape, by a substantially parallel change of shape of the two tube walls in contact with each other. Accordingly, the first opening of the air passage and the subsequent further opening of the air passage take place very gradually. This makes it possible to achieve a very sensitive metering of the pressure release which is maintained over a desirably large operating displacement of the pressure member. In addition, the increase of the air passage is that much greater at a later point, so that, following the determination of the diastolic pressure, the desirable rapid and thorough evacuation of the measuring cuff is obtainable in the same simple manner.

Similar relationships exist in a second embodiment in which the valve tube is pressed into the cavity of a longitudinal groove by the rounded extremity of the pressure member. During the closing and opening displacements, the valve tube is deformed in a way which is similar to the one described above.

The air release valve of the invention offers particularly favorable conditions in connection with the deformation characteristics of the walls of the valve tube involved. The air release valve also offers easy operability of the valve and of its pressure member through the use of a pivot lever, the latter making it possible to achieve an anatomically favorable position and orientation of the touch surface, in addition to correspondingly favorable displacement characteristics. A further advantage results from a displacement translation between the touch surface and the pressure member. The magnified displacement of the touch surface relative to the displacement of the pressure member further enhances the metering sensitivity. The invention further suggests the use of a leaf spring which is easy to install, its inner leg portion being simply placed into the positioning recess of the valve housing, prior to the attachment of the pivot lever which, when installed, retains the spring under a predetermined preload. the use of a second leaf spring under the valve tube itself makes is possible to return the valve tube more easily and more quickly to its original shape, after the pressure member is lifted from it. This applies particularly to a case in which the air release valve is inadvertently or intentionally left closed over an extended period of time, during which the elasticity characteristics of the valve tube may have deteriorated somewhat.

A second preferred embodiment of an air release valve offers a simplified manufacture and also a simple guidance for the pressure member. With this air release valve, it is possible to achieve particularly favorable conditions of deformation and displacement by assuring a good positioning of the valve tube which, in turn, guarantees that the cooperating elements maintain their proper operating positions, even under unfavorable operating conditions, or under clumsy manipulation. On the other hand, the removable valve cover facilitates the manufacture and assembly of all parts. This applies to both the initial assembly operation as well as to later repair and servicing work, as when the valve tube needs to be replaced, due to aging of its material.

In an air release valve in accordance with the present invention, the valve tube is elastically stretched. This causes the valve tube to more easily and more quickly leave the depression in the housing groove, when the pressure member is retracted, and it also causes the upper tube wall in contact with the pressure member to follow the displacements of the pressure member without lagging behind.

In a modification of the air release valve which involves the use of a cam face on the pivot lever, the valve is also then closing reliably, when greater manufacturing and/or assembly tolerances are encountered on the various cooperating parts. These tolerances are then compensated for by the initial relative lost-motion displacement.

BRIEF DESCRIPTION OF THE DRAWINGS

In the following, the invention is described in greater detail with reference to the accompanying drawings which illustrate, by way of example, several embodiments of the invention represented in the various figures as follows.

DESCRIPTION OF THE PREFERRED EMBODIMENTS

Figure 3:
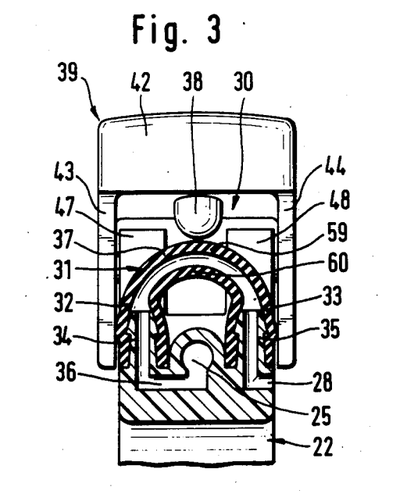
FIGS. 3 and 4 show, in two similar transverse cross sections, the air release valve of FIG. 1 in two different operating positions.
Figure 4:
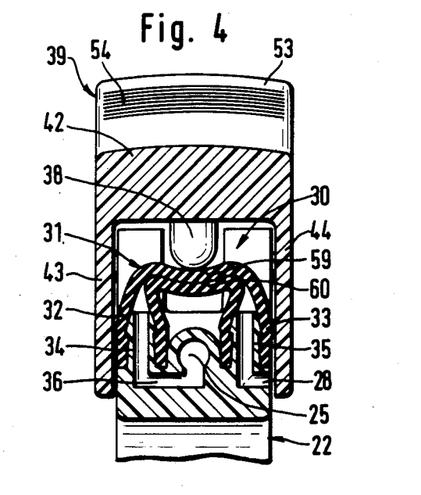

In the first embodiment of the invention, illustrated in FIGS. 1 through 6, the air release valve 21 comprises a valve housing 22 in the form of an injection-molded plastic part of approximately cube-shaped outline. The two longitudinal extremities of the valve housing 22 form air connections. The rear connector 23 on the left-hand side in FIG. 1 serves for the attachment of an inflation bulb (not shown). The front connector 24 on the right-hand side serves for the attachment of a pressure hose which links the air release valve 21 to an inflatable measuring cuff and, in most cases, also to a pressure gauge. An air duct 25 leads through the length of the valve housing 22 opening at the extremities of its rear and front connectors 23 and 24. The air duct 25 consists of two length portions of different diameter. The rearward duct portion 26 which begins at the rear connector 23 has a larger inner diameter, and the forward duct portion 27 which terminates at the front connector 24 has a smaller inner diameter. The valve housing 22 also has an outlet port 28 on one of its longitudinal sides (FIGS. 3 and 4). A flow metering device 30 is arranged between the air duct 25 and the outlet port 28.

The flow metering device 30 features a short length of tubing forming a valve tube 31, the two end portions 32 and 33 of the valve tube 31 being engaged over an inlet spout 34 and an outlet spout 35. The latter are integral portions of the valve housing 22. The two spouts 34 and 35 are arranged on the upper side of the valve housing 22, in a common transverse plane and at a lateral distance from each other. The distance between the outermost points of the two spouts 34 and 35 is smaller than the width of the valve housing 22 by at least twice the wall thickness of the valve tube 31. The two spouts 34 and 35 are at least approximately in parallel alignment with each other.

The inlet spout 34 communicates with the air duct 25 via a connecting duct 36 which extends through the valve housing 22. The outlet spout 35 communicates with the outlet port 28 which is open to the atmosphere.

As can be seen in FIG. 3, the valve tube 31 forms a free arcuate portion 37 between the inlet spout 34 and the outlet spout 35. The height of the arc defined by the arcuate portion 37 is approximately one-half of the distance between the axes of the two spouts 34 and 35. On the side of the arcuate portion 37 facing away from the spouts 34 and 35 is arranged a squeeze button 38 as part of a pivot lever 39. The squeeze button 38 has a rounded outer surface which is preferably of hemispherical shape.

The pivot lever 39 serves as a guide for the squeeze button 38. It is pivotably attached to the valve housing 22 by means of a pivot shaft 41 which extends parallel to the transverse plane of the arcuate portion 37 and spouts 34 and 35. The pivot lever 39 has a generally U-shaped cross section (FIGS. 3 and 4). Its somewhat plate-like bridge portion 42 is comparatively heavy. The lateral edges of the bridge portion 42 are adjoined by two thinner side walls 43 and 44. The inner distance between the two side walls 43 and 44 is at least equal to, and preferably somewhat great than, the width of the valve housing 22. The pivot shaft 41 is arranged at a certain distance from the bridge portion 42, being attached to the two side walls 43 and 44 as an integral extension thereof and thereby serving as a transverse bracing member.

The pivot shaft 41 is received in two pivot bearings 45 and 46 which are arranged on the upper side of the valve housing 22 in two comparatively wide longitudinal ridges 47 and 48 with parallel flanks. The two pivot bearings 45 and 46 are both shaped as split-shell bearings, their bearing shells being separated by a transverse through-slot 49. As a result of the slot 49, the two bearing shells can undergo a small elastic deformation, so that it becomes possible, during assembly, to forcibly snap the pivot shaft 41 of the pivot lever 39 into the pivot bearings 45 and 46, where the pivot shaft 41 is resiliently retained between the two bearing shells.

The squeeze button 38 forms an integral extension of the pivot lever 39 on the inner side 51 of its bridge portion 42 in alignment with the longitudinal center plane of the pivot lever 39. In the longitudinal sense, the squeeze button 38 is arranged on the forward side of the pivot shaft 41, its axis being oriented perpendicular to the pivot shaft 41 and at a predetermined distance therefrom. On the longitudinally rearward side of the pivot shaft 41, the bridge portion 42 has a greater length. Its outer side 52 is slightly convex in the shape of a cylinder section, the axis of which coincides with the longitudinal center plane of the valve housing 22. A portion of the outer side 52 of the bridge portion 42 which is distant from the pivot shaft 41 forms a touch surface 53 of the pivot lever 39. It preferably has transversely oriented serrations 54, as can be seen in FIG. 4. Instead of, or in addition to, the serrations 54, the outer side 52 may also have a concave depression in the area of the touch surface 53.

Figure 1:
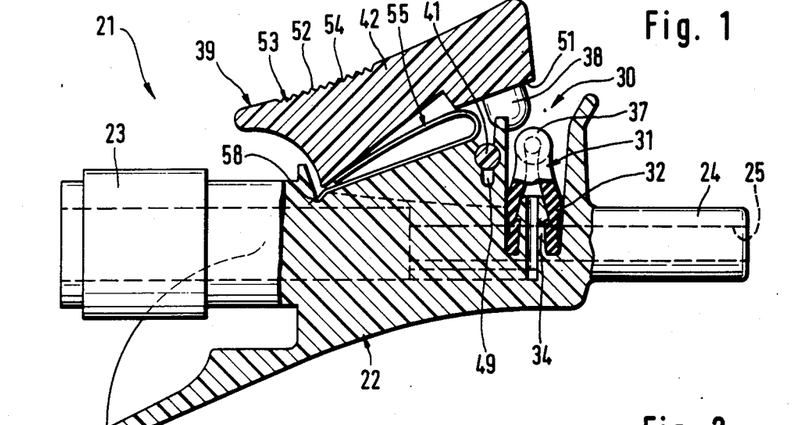
FIG. 1 shows a longitudinal sectional of an air release valve representing a first embodiment of the invention, the section being taken along line I—I in FIG. 2.
Figure 2:
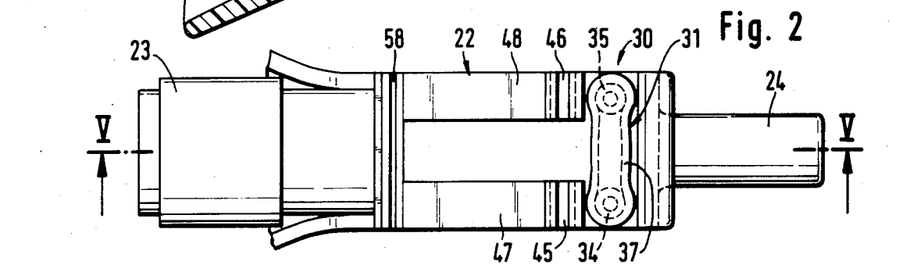
FIG. 2 shows the air release valve of FIG. 1 in a plan view, with the control lever removed.
Figure 5:
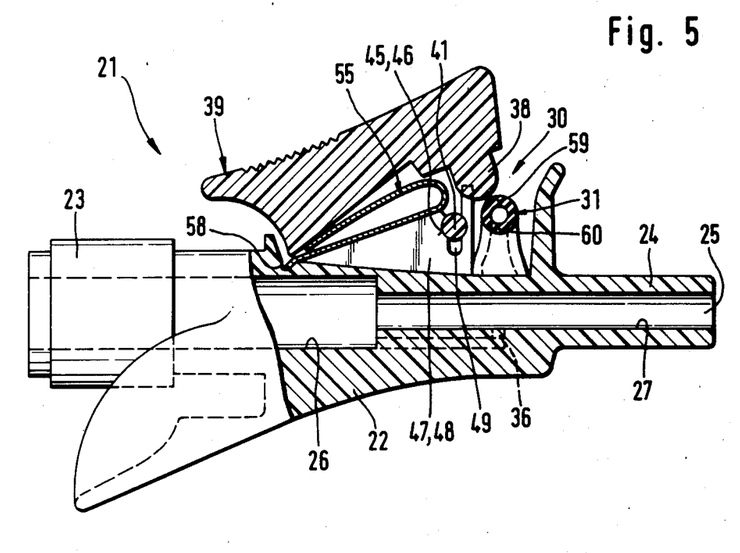
FIGS. 5 and 6 show, in two longitudinal sections taken along line V—V in FIG. 2, the air release valve in two different operating positions.

When the air release valve 21 is in its open position, the pivot lever 39 assumes a position which is shown in FIGS. 1 and 5. In the closed valve position, the pivot lever 39 assumes a position which can be seen in FIG. 4. The pivot lever 39 is biased into this position by means of a leaf spring 55 which thereby serves as a closing spring for the air release valve 21. The leaf spring 55 has a U-shaped outline with two leg portions 56 and 57. The inner leg portion 56 has a slightly kinked extremity with which it engages a recess 58 of the valve housing 22. The outer leg portion 57 of the leaf spring 55 bears freely against the inner side 51 of the bridge portion 42 of the pivot lever 39, the leaf spring 55 being laterally retained between the side walls 43 and 44 of the pivot lever 39.

In view of the fact that the leaf spring 55 is mounted with a certain bending preload, it is reliably positioned by its kinked extremity engaging the recess 58 of the valve housing 22 and its outer leg portion 57 bearing against the inner side 51 of the pivot point lever 39.

A detent mechanism, not shown in the drawing, retains the pivot lever 39 in its open position (FIGS. 1 and 5). As part of this detent mechanism, the valve housing 22 includes on each of its two side walls a detent groove and the two side walls 43 and 44 of the pivot lever 39 have on their inner sides cooperating detent ridges which are so arranged that in the open position of the pivot lever 39 they engage the detent grooves. This detent mechanism is arranged in an area of the pivot lever 39 which is distant from its pivot shaft 41.

Figure 6:
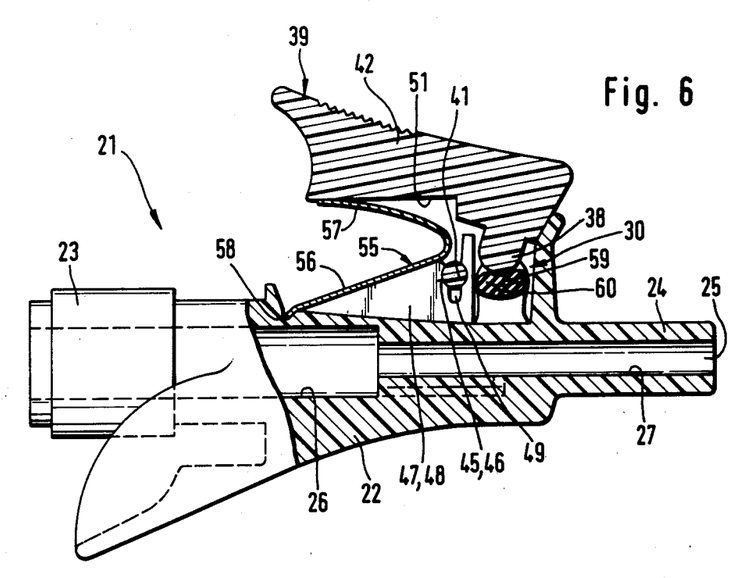
Figure 7:
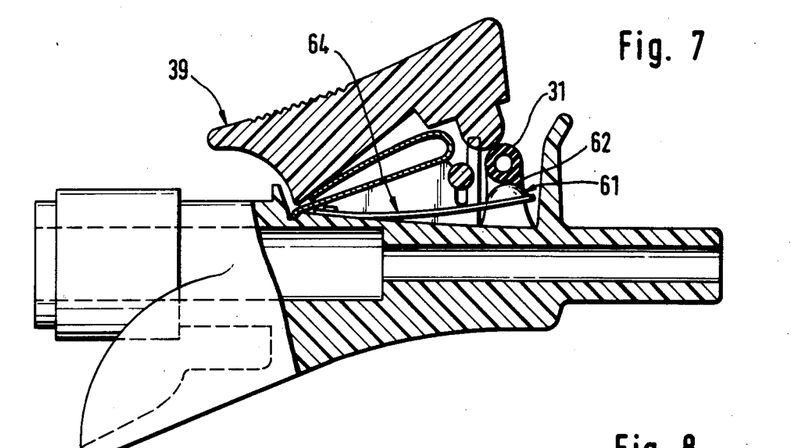
FIG. 7 shows a longitudinal section of a modified air release valve embodying the invention, the section being taken along line VII—VII in FIG. 8.
Figure 8:
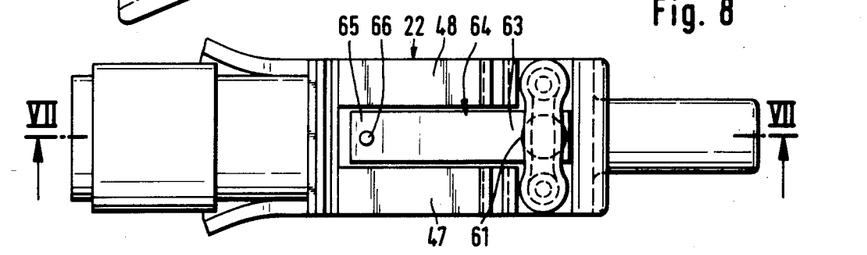
FIG. 8 shows the air release valve of FIG. 7 in a plan view, with the control lever removed.
Figure 9:
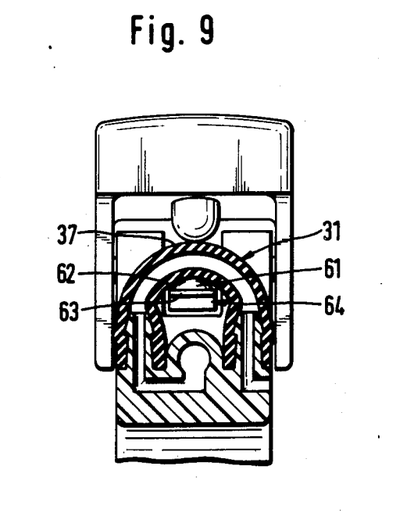
FIGS. 9 and 10 show, in two similar transverse cross sections, the air release valve of FIG. 7 in two different operating positions.
Figure 10:
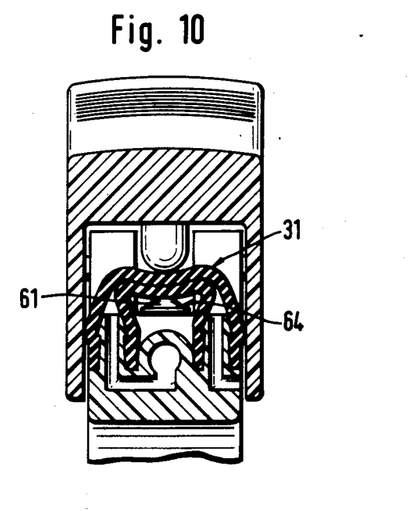

In the open position of the air release valve 21, the valve tube 31 extends freely between the two spouts 34 and 35 in the form of an arcuate portion 37 (FIG. 3). When the pivot lever 39 is released from its detent mechanism, and as it is pivoted towards its closed position under the influence of the leaf spring 55, the squeeze button 38 presses gainst the arcuate portion 37 in the plane of the latter, thereby collapsing the arcuate portion 37 inwardly from its original arcuate contour (FIG. 4), while the upper tube wall 59 of the arcuate portion 37 is cross-sectionally deformed into an opposite curvature (FIG. 6), due to the rounded surface of the squeeze button 38. As these two deformations take place, the upper tube wall 59 of the arcuate portion 37 enters into intimate contact with the lower tube wall 60, so as to completely close off the cavity of the valve tube 31 at this point, without exerting a squeezing action on the tube walls (FIGS. 4 and 6).

When the pivot lever 39 is moved towards its open position, in opposition to the closing bias of the leaf spring 55, the collapsed portion of the valve tube 31 follows the retreating squeeze button 38, due to the elasticity of the tube material. As the upper tube wall 59 of the valve tube 31 undergoes a corresponding erection deformation, the cavity of the arcuate portion 37 is opened very gradually, while the lower tube wall 60 continues to follow the retraction movement of the squeeze button 38, due to the elasticity of the valve tube 31. Only after a predetermined distance of return movement of the squeeze button 38 does the lower tube wall 60 start lagging behind the upper tube wall 59, so that the flow section of the cavity inreases more rapidly and a quick-release or dumping of the entire pressurized air volume contained in the measuring cuff, connecting line and air release valve 21 takes place.

FIGS. 7 through 11 show the air release valve 21 of the invention in a slightly modified embodiment featuring the addition of a valve release button 61. All the other parts of the air release valve 21 are the same as described above.

The valve release button 61 is arranged underneath the arcuate portion 37 of the valve tube 31. On the side facing towards the arcuate portion 37, the leaf spring 64 has a rounded contact face. The valve release button 61 is attached to the free extremity of a leaf spring 64 which is arranged in the channel-shaped space between the flanks of the two longitudinal ridges 47 and 48 on the upper side of the valve housing 22. The other extremity of the leaf spring 64 engages the bottom of the channel, where it is attached by means of an integral rivet 66 which is provided for this modification on the valve housing 22.

The shape of the leaf spring 64 is such that, in the open position of the pivot lever 39 (FIG. 7), it retains a certain residual tension. When the pivot lever 39 is pivoted into the closed position (FIG. 11) and its squeeze button 38 collapses the valve tube 31 by pressing it downwardly against the valve housing 22, the valve release button 61 on the leaf spring 64 yields elastically underneath the valve tube 31, while the tension of the leaf spring 64 increases. As the pivot lever 39 is moved out of its closed position through a pivoting movement in the direction towards its open position, the valve release button 61 assures, under the return force of the leaf spring 64, that the valve tube 31 follows the movement of the squeeze button 38 immediately by undergoing an erection at the rate permitted by the position of the squeeze button 38.

In the place of the valve release button 61 which is supported on the valve housing 22, the erection of the arcuate portion 37 can also be assisted by arranging a special release arm on the underside of the pivot lever 39, as an attachment to, or an integral part of, the pivot lever 39. This arm is so arranged that it reaches underneath the arcuate portion 37 and loosely touches its underside in the erected position of the valve tube 31. In the collapsed position of the arcuate portion 37, the release arm does not touch the arcuate portion 37, but, as soon as the pivot lever 39 is moved a certain distance from its closed position towards the open position, the release arm engages the underside of the arcuate portion 37, thereby preventing a situation in which the arcuate portion 37 does not immediately follow the return movement of the squeeze button 38.

Figure 11:
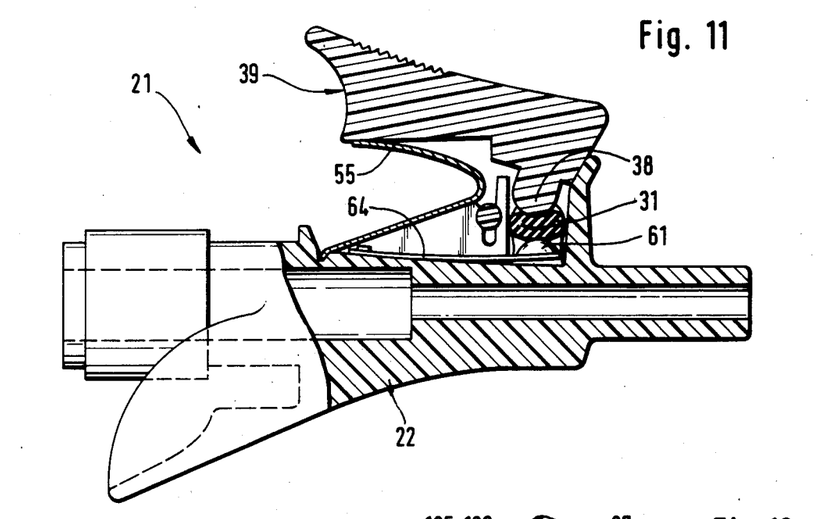
FIG. 11 shows, in a longitudinal section, the air release valve of FIG. 7 in a different operating position.

As can be seen in FIGS. 6 and 11, an upstanding wall portion of the valve housing 22 serves as an abutment for the pivot lever 29 in the released position of the latter. This abutment limits the deformation of the valve tube 31 in the closed valve position.

In the following will be described a second embodiment of the invention in the form of an air release valve 71 which is illustrated in FIGS. 12 through 20. To the extent that components or component groups are not described separately in this description, it is to be assumed that they are identical or at least similar to the corresponding components or component groups of the above-described first embodiment.

The valve housing 72 again forms a rear connector 73 and a front connector 74 which serve for the connection of an inflation bulb and of a pressure hose, respectively. Extending through the interior of the valve housing 72 is an air duct 75 of which the rearward duct portion 76 and the forward duct portion 77 have different diameters. Branching off at an acute angle from the rearward duct portion 76 is an outlet duct 78 which terminates in an outlet port 79.

The flow metering device 80 which is arranged in the outlet duct 78 features a short length of a valve tube 81. The inlet extremity 82 of the latter engages an inlet spout 83 which extends from the valve housing 72 in the longitudinal center plane thereof, forming a portion of the outlet duct 78. The opening of the outlet extremity 84 of the valve tube 81 forms the outlet port 79 of the air release valve 71.

Figure 12:
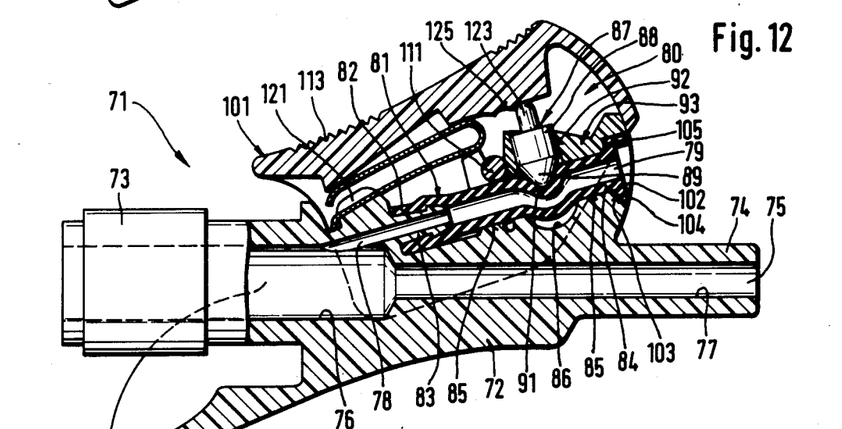
FIG. 12 shows a longitudinal section of an air release valve representing a second embodiment of the invention.
Figure 13:
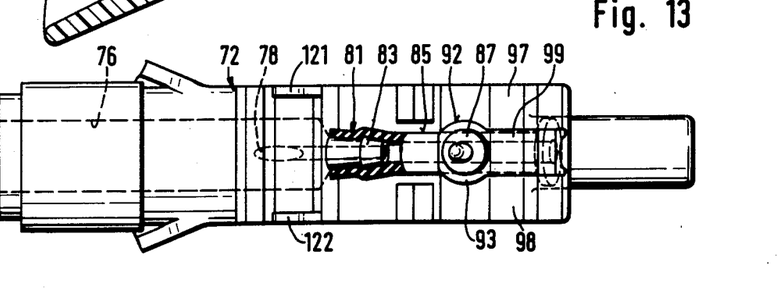
FIG. 13 shows the air release valve of FIG. 12 in a plan view, with the control lever removed.
Figure 14:
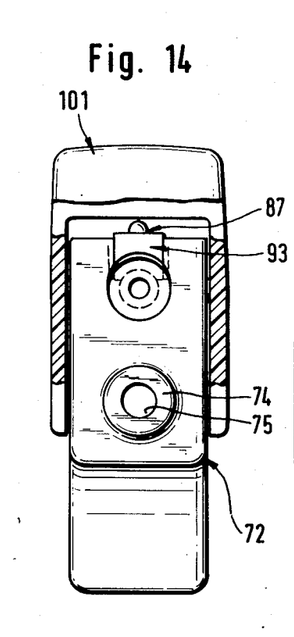
FIG. 14 shows the air release valve of FIG. 12 in an end view.
Figure 16:
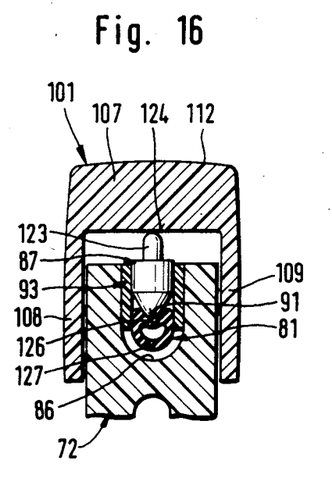
FIGS. 16 and 17 show, in two similar transverse cross sections, the air release valve of FIG. 12 in two different operating positions.

At a certain distance from the inlet spout 83, the valve housing 72 defines an upwardly open housing groove 85 of semicylindrical shape, the width of which corresponds to the diameter of the valve tube 81. In the area of the housing groove 85 is further arranged a depression 86 (FIGS. 12 and 16). It has the contour of a body of rotation, preferably of a spherical cavity, and its center axis intersects the axis of the housing groove 85 at right angles. The width of the depression 86 is at least equal to one-half of the circumference of the valve tube 81.

Engaging the valve tube 81 from the side opposite the depression 86 is a squeeze button 87 in the form of a body of rotation with a guide portion 88 and a tapered head portion 89, the point of which is rounded, preferably with a spherical contour, to form a pressure surface 91 which cooperates with the valve tube 81. The center axis of the squeeze button 87 is aligned with the axis of the depression 86. The pressure surface 91 of the squeeze button 87 is at least approximately concentric with the surface of the depression 86 in the closed valve position (FIG. 15) in which the valve tube 81 is deformed into the depression 86 and at which point the distance between the pressure surface 91 and the depression 86 is at least approximately equal to twice the wall thickness of the valve tube 81.

Figure 18:
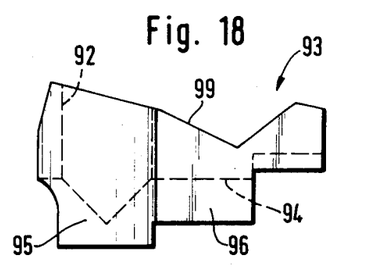
FIGS. 18 through 20 show different views of a cover for the air release valve of FIG. 12.
Figure 19:
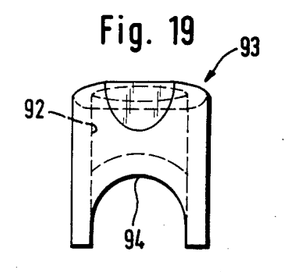
Figure 20:
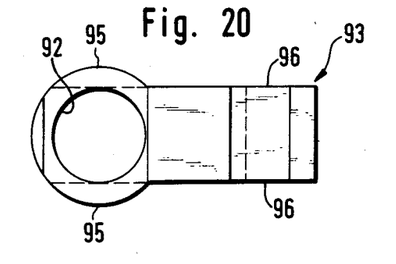

The squeeze button 87 is guided by a valve guide 92 with a cylindrical bore cooperating with the guide portion 88 of the squeeze button 87. The valve guide 92 is an integral part of a valve cover 93 which covers the housing groove 85 (FIGS. 18 through 20). Viewed in the longitudinal direction of the valve tube 81, the valve cover 93 starts at a certain distance form the inlet spout 83, at least no later than the edge of the depression 86. From there, it extends to a point beyond the outlet extremity 84 of the valve tube 81. On its underside, the valve cover 93 has a semi-cylindrical cover groove 94 which complements the housing groove 85 of the valve housing 72 and which is likewise fitted to the outer surface of the valve tube 81.

The two side walls of the valve cover 93 have cylindrical side wall portions 95 and flat side wall portions 96. The cylindrical side wall portions 95 are arranged concentrically with the cylindrical bore of the valve guide 92. Their outer radius is equal to the radius of the depression 86 in the housing groove 85. The width of the valve cover 93 at its two flat side wall portions 96 is smaller than the maximum width at its two cylindrical side wall portions 95. As a result, the cylindrical side wall portions 95 serve to position the valve cover 93 in the longitudinal sense by providing a reliable seating engagement with the valve housing 72. In the area of the flat side wall portions 96, the valve cover 93 is positioned in the lateral sense by engaging the inner flanks of two housing walls 97 and 98 which project from the upper side of the valve housing 72 on opposite sides of the housing groove 85 to a certain height above the latter. The housing walls 97 and 98 also form the cylindrical positioning faces for the cylindrical side wall portions 95 of the valve cover 93.

The upper side 99 of the valve cover 93, when seen from the side, has the same contour as the two housing walls 97 and 98. At least a portion of it is fitted to the contour of the underside of the pivot lever 101, when the latter is in its closed position (FIG. 15).

Figure 15:
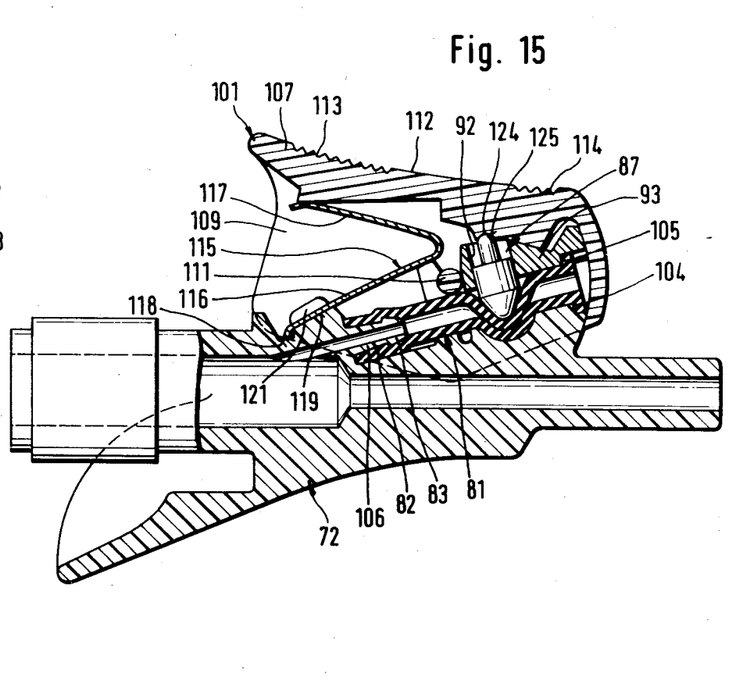
FIG. 15 shows, in a longitudinal section, the air release valve of FIG. 12 in a different operating position.

As can be seen in FIGS. 12 and 15, the valve tube 81 has on its outlet extremity 84 a peripheral collar 102, forming an annular shoulder 103 in its rear axial side. Cooperating with the shoulder 103 are an abutment face 104 on the valve housing 72 and an abutment face 105 on the valve cover 93. The two aligned abutment faces 104 and 105 are arranged at a distance from the spout base 106 of the inlet spout 83 which is greater than the distance of the shoulder 103 of the collar 102 from the inlet extremity 82 of the valve tube 81. This difference in axial length is selected in accordance with the elasticity of the valve tube 81, being smaller for a greater elasticity of the valve tube 81. For a small elasticity, it may amount to as much as 1.5 mm, for example.

In the place of the described fixed length difference, the intended purpose of obtaining an elastic elongation of the valve tube 81 can also be achieved by choosing the distance of the shoulder 103 of the collar 102 of the valve tube 81 to be equal or greater than the distance of the abutment faces 104 and 105 from the inlet spout 83 and by inserting between the shoulder 103 and the abutment faces 104 and 105 a spring, preferably a helical compression spring.

The pivot lever 101 is similar to the pivot lever 39 of the first embodiment, having a U-shaped cross section with a bridge portion 107 which is adjoined by two side walls 108 and 109. The pivot shaft 111 of the pivot lever 101 extends perpendicularly to the longitudinal axis of the valve tube 81. Its extremities are integrally attached to the inner sides of the two side walls 108 and 109. The outer surface on the upper side of the pivot lever 101 forms a slightly curved touch surface 112 in the shape of a cylinder section, the axis of which coincides with the longitudinal center plane of the valve housing 72. A portion of the touch surface 112 is provided with transverse serrations 113. Similar transverse serrations 114 are also arranged on the other axial end of the upper surface of the pivot lever 101, on the opposite side of the pivot shaft 111.

A U-shaped leaf spring 115 is again used to bias the pivot lever 101 into the closed valve position, the inner leg portion 116 of the leaf spring 115 pressing against the upper side of the valve housing 72, while the outer leg portion 117 presses against the inner side of the bridge portion 107 of the pivot lever 101. The inner leg portion 116 of the leaf spring 115 has a slightly kinked extremity with which it engages a positioning recess 118 of the valve housing 72. An adjoining portion of the inner leg portion 116 is positioned in a flat positioning groove 119, between opposing lateral guide flanks 121 and 122 (FIG. 13) of the valve housing 72.

The pressure member 87 includes, on its axial end facing away from the valve tube 81, a follower pin 123 with a rounded crown surface 124. On the inner side of the pivot lever 101, in the area of engagement with the follower pin 123 and along the relative displacement path of the crown surface 124 of the follower pin 123, is arranged a cam face 125. At the point along the cam face 125 which corresponds to the closed position of the pressure member 87 (FIG. 15) and in the immediately adjacent portion of the cam face 125, the cam incline is so slight that the opening movement of the pressure member 87 lies within the elastic deformation of the still closed valve tube 81. An adjoining portion of the cam face 125 is inclined in such a way the the cross-sectional increase of the cavity of the valve tube 81 is small at the beginning and increases progressively thereafter.

Figure 17:
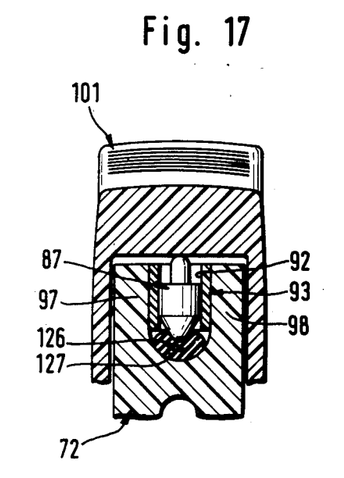

The open valve position of the pivot lever 101 which can be seen in FIG. 12 is also a rest position in which it is retained by a detent mechanism (not shown). As the pivot lever 101 is moved away from this rest position and its portion forward of the pivot shaft 111 pivots in a clockwise direction, the pressure member 87 is advanced downwardly against the valve tube 81, as the result of its follower pin 123 cooperating the cam face 125. In this process, the upper tube wall 126 of the valve tube 81 (FIG. 16) in contact with the pressure member 87 is progressively collapsed and pushed against the opposite lower tube wall 127 overlying the depression 86. The collapsing action of the upper tube wall 126 takes place both in the longitudinal center plane (FIGS. 12 and 15) and in the cross-sectioal plane (FIG. 16). No later than when the collapsing upper tube wall 126 reaches the lower tube wall 127 and actually sooner than that due to the overall deformation resistance of the tube walls, the lower tube wall 127 is bulged downwardly, at least in the longitudinal center plane, until the two tube walls 126 and 127 finally engage each other in intimate contact, while both are deflected deep into the depression 86 (FIGS. 15 and 17). This spatial deformation of the upper tube wall 126, and the consequent deformation of the lower tube wall 127, produce a complete closure of the cavity inside the valve tube 81, without exerting a squeezing action on the tube walls.

In the course of the opening movement of the pivot lever 101 and pressure member 87 away from their closed valve positions (FIG. 15), the two tube walls 126 and 127, in close contact with each other, follow both initially the displacements of the pressure member 87 in an elastic response. Later, the cavity of the valve tube 81 is first opened very gradually, the opening displacement inreasing rapidly thereafter.

FIG. 15 also shows that, in the closed position of the pivot lever 101, the latter abuts against the upper side of the valve cover 93, thereby limiting the deformation of the valve tube 81 in the closed valve position.

It is to be understood that the invention is not limited in its application to the details of construction and arrangement of parts illustrated in the accompanying drawings, since the invention is capable of other embodiments and of being practiced or carried out in various ways. It is also to be understood that the phraseology or terminology employed herein is for the purpose of description and not of limitation.

I claim the following:

1. An air release valve for a sphygmomanometer having an inflatable measuring cuff and a source of air pressure, the air release valve comprising in combination:

a valve housing;
an air duct extending through the valve housing, one end of the air duct being connectable to the source of air pressure, and the other end of the air duct being connectable to the measuring cuff;
an outlet duct branching off the air duct in the valve housing and leading to the atmosphere via an outlet port;
a valve tube forming a length portion of the outlet duct, the valve tube being of a material which is capable of resilient cross-sectional deformation, until opposite wall portions of the valve tube press against each other to close the outlet duct;
a pressure member associated with the valve housing in such a way that the pressure member is movable in a direction which is substantially perpendicular to the centerline of the valve tube, along a path which intersects said centerline;
means for biasing the pressure member towards a closed position in which the pressure member cross-sectionally deforms a portion of the valve tube to close the outlet duct; and
manually operable means for retracting the pressure member away from the valve tube, in opposition to the pressure member biasing means, so as to variably open the outlet duct and to release air therethrough at a controllable rate; and wherein
the vale tube is curved so that its centerline defines a substantially semi-circular arc;
the pressure member is movable against the valve tube from the outside of said semi-circular arc, its movement path being substantially in alignment with the plane defined by the arcuate centerline of the valve tube, and the point of intersection between said movement path and centerline being located in the midportion of said arc; and the size of the inner radius of the arcuate valve tube in relation to the wall thickness of the valve tube is such that the bending resistance of the tube wall on the inner side of said arc in opposition to a closing movement of the pressure member is sufficient to effect closure of the valve tube under inward-deflection of the valve tube from its arcuate outline, whereby said tube wall on the inner side of said arc is not supported by a supporting member and the valve tube is closed without a squeezing action on its walls.

2. An air release valve as defined in claim 1, wherein the valve housing includes, as part of the outlet duct, two connecting formations to which the two extremities of the valve tube are attached, said connecting formations having longitudinal centerlines which are oriented substantially parallel to each other and to the path of the pressure member; and said connecting formations of the valve housing support the valve tube against the closing force exerted against the valve tube by the pressure member.

3. An air release valve as defined in claim 2, wherein the two connecting formations are connecting spouts to which the extremities of the valve tube are attached by extending over the connecting spouts, under resilient radial expansion of the valve tube in the areas of attachment; and the two connecting spouts are integral extensions of the valve housing.

4. An air release valve as defined in claim 1, wherein the pressure member retracting means includes a pivot lever which is pivotably supported by the valve housing on a pivot axis which extends substantially parallel to said plane defined by the arcuate centerline of the valve tube and is oriented substantially perpendicularly to the movement path of the pressure member; the pressure member is operatively connected to the pivot lever; and the pressure member biasing means is a spring engaging the pivot lever so as to urge it into the closed valve position.

5. An air release valve as defined in claim 4, wherein the pressure member biasing means is a U-shaped leaf spring arranged between the valve housing and the pivot lever, on the opposite side of the pressure member with respect to the pivot axis of the pivot lever; and one leg portion of the leaf spring is positioned in a positioning recess of the valve housing, and the other leg portion of the leaf spring bears against the pivot lever in a direction away from the valve housing.

6. An air release valve as defined in claim 4, wherein the pressure member is fixedly connected to the pivot lever, the movement path of the pressure member being defined by a radius around the pivot axis of the pivot lever; and the plane defined by the arcuate centerline of the valve tube is substantially coincident with a tangent to the path of the pressure member, at a point along said path with substantially corresponds to the closed position of the pressure member.

7. An air release valve as defined in claim 4, further comprising
abutment means defined between the valve housing and the pivot lever for determining the position of the pivot lever in the closed valve position, said abutment-determined position of the pivot lever being located a distance beyond the position of the pivot lever in which the valve tube is just completely closed under cross-sectional deformation by the pressure member.

8. An air release valve as defined in claim 1, further comprising
spring means resiliently supporting the valve tube from the inner side of its arcuate outline, in opposition to the valve closing force of the pressure member, the spring means being operable to assist the valve tube in recovering from its internally closed, deflected outline to its internally open, arcuate outline.

9. An air release valve for a sphygmomanometer having an inflatable measuring cuff and a source of air pressure, the air release valve comprising in combination:
a valve housing;
an air duct extending through the valve housing, one end of the air duct being connectable to the source of air pressure, and the other end of the air duct being connectable to the measuring cuff;
an outlet duct branching off the air duct in the valve housing and leading to the atmosphere via an outlet port;
a valve tube forming a length portion of the outlet duct, the valve tube being of a material which is capable of resilient cross-sectional deformation, until opposite wall portions of the valve tube press against each other to close the outlet duct;
a pressure member associated with the valve housing in such a way that the pressure member is movable in a direction which is substantially perpendicular to the centerline of the valve tube, along a path which intersects said centerline;
means for biasing the pressure member towards a closed position in which the pressure member cross-sectioally deforms a portion of the valve tube to close the outlet duct; and
manually operable means for retracting the pressure member away from the valve tube, in opposition to the pressure member biasing means, so as to variably open the outlet duct and to release air therethrough at a controllable rate; and wherein
the valve tube is a substantially straight tube having its two extremities longitudinally confined by the valve housing;
the valve housing includes a surface supporting the valve tube on the side which is opposite the side on which the pressure member moves against the valve tube;
the valve tube supporting surface includes an interruption in the form of a depression in the supporting surface, said surface depression being aligned longitudinally with the region in which the vale tube is cross-sectionally deformed by the pressure member, the surface depression allowing the pressure member to deflect the entire valve tube from its normally straight outline, so as longitudinally stretch the cross-sectionally deformed portion of the valve tubein the closed position of the pressure member, whereby the valve tube is closed without a squeezing action on its walls.

10. An air release valve as defined in claim 9, wherein the valve housing includes, as part of the outlet duct, a connecting formation to which one extremity of the valve tube is attached; and the other extremity of the valve tube serves as the outlet port of the outlet duct.

11. An air release valve as defined in claim 10, wherein the connecting formation of the valve housing is a connecting spout in the form of an integral extension of the valve housing which is axially aligned with the valve tube, the attached extremity of the valve tube extending over the connecting spout, under resilient radial expansion of the valve tube in the area of attachment; and the outlet port extremity of the valve includes a radial collar which cooperates with an outwardly facing end face of the valve housing to provide said longitudinal confinement of the vale tube extremities.

12. An air release valve as defined in claim 9, wherein the pressure member retracting means includes a pivot lever which is pivotably supported by the valve housing on a pivot axis which extends substantially perpendicularly to the centerline of the valve tube and to the movement path of the pressure member;

the pressure member is operatively connected to the pivot lever; and the pressure member biasing means is a spring engaging the pivot lever so as to urge it into the closed valve position.

13. An air release valve as defined in claim 12, wherein the pressure member biasing means is a U-shaped leaf spring arranged between the valve housing and the pivot lever, on the opposite side of the pressure member with respect to the pivot axis of the pivot lever; and one leg portion of the leaf spring is positioned in a positioning recess of the valve housing, and the other leg portion of the leaf spring bears against the pivot lever in a direction away from the valve housing.

14. An air release valve as defined in claim 12, further comprising abutment means defined between the valve housing and the pivot lever for determining the position of the pivot lever in the closed valve position, said abutment-determined position of the pivot lever being located a distance beyond the position of the pivot lever in which the valve tube is just completely closed under cross-sectional deformation by the pressure member.

15. An air release valve as defined in claim 9, wherein the supporting surface of the valve housing is in the form of a supporting groove which has a semi-circular cross section matching the diamter of the valve tube; and the valve housing includes a valve cover with a complementary cover groove of semi-circular cross section, the supporting groove of the valve housing and the cover groove of the valve cover surrounding at least a length portion of the valve tube.

16. An air release valve as defined in claim 15, wherein the pressure member has a spherically rounded extremity with which it engages the valve tube to effect said cross-sectional deformation of the valve tube; and the depression in the supporting surface of the valve housing is in the form of a concave recess having a radius which, in the closed position of the pressure member, is substantially concentric to the radius of the rounded extremity of the pressure member and spaced therefrom a distance no less than twice the wall thickness of the valve tube.

17. An air release valve as defined in claim 15, wherein the pressure member is a body of rotation; and the valve cover has a guide bore guiding the pressure member for linear valve closing and opening movements.

18. An air release valve as defined in claim 17, wherein the pressure member retracting means includes a pivot lever which is pivotably supported by the valve housing on a pivot axis which extends substantially perpendicularly to the centerline of the valve tube and to the movement path of the pressure member;

the pivot lever bears against the pressure member in the sense of valve closing, under the action of the pressure member biasing means, the pivot lever has a cam face along which the point of contact between the pivot lever and the pressure member shifts, as the pivot lever and the linearly guided pressure member move between their closed and open valve positions; and the cam face of the pivot lever is so arranged that an initial opening displacement of the pressure member requires a relatively magnified angular movement of the pivot lever.

* * * * *